US00PP08962P

United States Patent [19]

Klemm

[11] Patent Number: Plant 8,962

[45] Date of Patent: Oct. 25, 1994

[54] GERANIUM NAMED KLEGOM

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 172,619

[22] Filed: Dec. 23, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by its compact and harmonical growth, lavender pink flowers with a red center and medium green leaves, having early precocity and good weather resistance.

1 Drawing Sheet

BACKGROUND OF THE NEW PLANT

The present invention comprises a new and distinct cultivar of geranium, botanically known as *Pelargonium zonale*-Hybride. The new cultivar is propagated from cuttings resulting from the cross of SEL "Klecerol" (U.S. Plant Pat. No. 7,140) and PAC "Penlau". Both "Klecerol" and "Penlau" are commercially available. "Klecerol is also known as SEL "Carol." "Penlau" is also known as PAC "Laura." SEL "Klecerol" is a geranium with pink petals having a white center, RHS 57-C and RHS 67-C, having early to medium early precocity, and small to medium growth height, 250–270 mm. SEL "Klecerol" grows compact and branches well. The large clusters of 100 to 110 mm. diameter stand 180 mm. long on stable stems above the healthy, medium green foliage which is slightly zonated. PAC "Penlau" has violet pink RHS 66-A, with early precocity and small growth habit of between 220–240 mm. in height in September. The characteristics of PAC "Penlau" are elegant, cupshaped flowers that stand on the dark-leaved plants. The parents are both available in our company. "Penlau" is bred by PAC Elsner in Dresden.

As a result of this cross the present cultivar was created in 1989 in Stuttgart, Germany and has been repeatedly asexually reproduced by cuttings in Stuttgart, Germany over a four year period. It has been found to retain its distinctive characteristics through successive propagations; and this novelty appears to be firmly fixed.

The new cultivar is distinguished from other pink varieties by its very nice lavender-pink with red center petals and its superior garden performance. The present cultivar is very floriferous (i.e., 491 flowers on three plants during one season). The flowers do not shatter or fade out, the medium green leaves can stand hot or wet weather.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to the R.H.S. Colour Chart of The Royal Horticultural Society of London.

THE PLANT

Classification:

*Botanical.*—*Pelargonium zonale*-Hybride.

*Commercial.*—Zonal geranium.

Parentage:

*Seed parent.*—SEL "Klecerol." (U.S. Plant Pat. No. 7,140).

*Pollen parent.*—PAC "Penlau".

Form: Bush.

Height of plant: 260–300 mm. in September.

Stalk length: 200–280 mm. in September.

Branching character: Very good branching.

Number of stems per stalk: 6 in June.

Number of stalks per plant: 8 in June.

Internode length: About 5–12 mm. depending on the light where the plant is propagated and the method of propagation.

Growth rate: If propagated in January the blooms can be sold in April, without pinching or Cyocel treatment.

Strength: Good cutting producer for propagation, and the plant performs very well after shipping as a rooted or unrooted cutting.

Zonation: The zonation is very weak and hardly visible.

Foliage:

*Quantity.*—Average amount of leaves.

*Size.*—80×40 mm.

*Shape.*—Kidney shaped.

*Margin.*—Bicrenate.

*Texture.*—Smooth.

Color Upper side: medium green, veins and center are a little lighter — RHS 137-B. Under side: light green — RHS 137-C.

Petioles:

*Length.*—About 40–50 mm., depending on the time of the year.

THE BUD

Size:

*Diameter.*—About 9 mm.
*Length.*—About 14–16 mm.
*Shape.*—Ovoid, with pointed apex, rather thick.
*Form.*—Pointed.
*Rate of opening.*—Medium.

Color: When sepals first divide they are pink and white RHS 68-B; when you watch the bud you see the reverse side. When petals begin to unfurl they are blueish pink RHS 68-A on the inside.

Sepals:
*Number.*—5.
*Shape.*—Long and pointed.
*Color.*—Inside — light green — RHS 146-C. Outside — light green — RHS 146-B.
*Form.*—Standing up.

Petiole of Floret:
*Length.*—About 22 mm.
*Strength.*—Erectly arranged hemispherically around the end of the cluster stalk.
*Color.*—Brown — RHS 183-B to green 146-B.
*Hairy.*—Very short hairs present on the petiole.

THE FLOWER

Blooming habit: Klegom blooms in April and then continuously and very profusely until the frost. The number of clusters per plant varied from 286 to 491 (on three plants) in trials depending on the length of time outside.

Size of floret: Approximately 47 mm×11–12 mm.

Borne: In a cluster having between about 33 to 61 florets per cluster.

Shape: When the bloom first opens the blooms are cut-shaped. The blooms change very little in shape.

Petals:
*Number.*—About five to seven per floret or flower.
*Arrangement.*—Petals are arranged around the ovaries.
*Form.*—Broad.
*Color.*—Outer petal: purple — RHS 72-C. Base: purple — RHS 75-C. Inside petal: purple — RHS 72-C. Base: purple 72-C. Big spots on all petals tyrian purple RHS 57-A and rose purple RHS 75-B. Reverse side: white — RHS 155-D.
*Pattern.*—The petals, and particularly the top, mature petals of each floret variably express a pattern which includes a darker purple blush-like spot in the central portion of the petal which effuses or bleeds, progressively, into the predominant purple color (RHS 72C) of the top surface. On the top upper petals, the spot is separated from the attachment point of the petal be a generally white, basal zone of substantially white color, except of the veins, which have the same color as the spot. These markings may be wholly or partly obscured by the overlying petaloids which may or may not express similar color markings without a white basal zone.

Texture: Soft.

Appearance: Satiny.

How long do petals remain on stem: About five days depending on the weather.

Petaloids:
*Number.*—About 2 to 3.
*Size.*—About 6 to 10 mm.
*Color.*—Pink — RHS 68-A.

Cluster stem:
*Length.*—90–120 mm.
*Color.*—Green — RHS 146-C.
*Characteristics.*—Sturdy and upright.

Persistence: No.

Disease resistance: The present cultivar does not suffer from Botrytis.

Weather resistance: The present cultivar is not unusually affected by wet or hot weather.

Lasting quality:
*On the plant.*—It takes 28 days between the opening of the first floret and the last floret of a whole cluster. If you do not pick off the matured flowers, the cluster looks lovely for about 19–20 days.
*As a cut flower.*—About 5–6 days.

Fragrance: No perceptible fragrance.

REPRODUCTIVE ORGANS

Stamens:
*Anthers.*—Seven positioned around the stigma with 2 mm length.
*Filaments.*—6–7 mm in length and white.

Pollen: Orange in color.

Pistils:
*Number.*—One.
*Length.*—Approximately 11 mm.

*Stigmas.*—Pink to red in color.

Ovaries: Green in color.

Fruit: Fertile.
*Shape.*—Ovoid.
*Color at maturity.*—RHS 176-C.

I claim:

1. A new and distinct geranium cultivar substantially as herein shown and described, particularly distinguished by its compact and harmonical growth, lavender pink flowers with a red center and medium green leaves, and early precocity and good weather resistance.

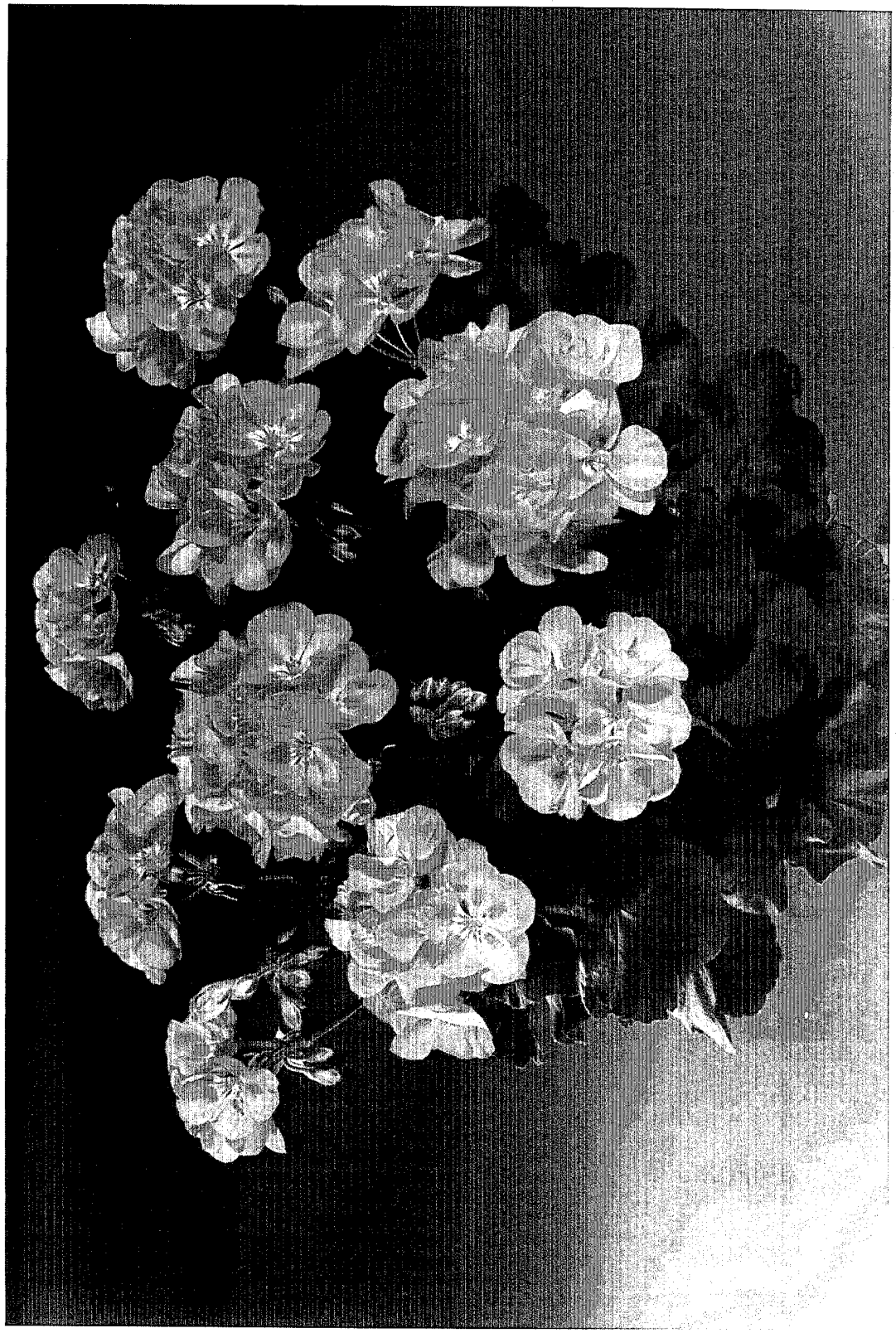

* * * * *